United States Patent
Fricke et al.

(10) Patent No.: US 8,249,715 B2
(45) Date of Patent: Aug. 21, 2012

(54) IMPLANTABLE MEDICAL DEVICE CONFIGURED AS A PEDOMETER

(75) Inventors: Jilliann G. Fricke, Clayton, NC (US); Lemont Baker, Raleigh, NC (US); Donald L. Hopper, Maple Grove, MN (US); Aaron R. McCabe, Minneapolis, MN (US); James A. Esler, Coon Rapids, MN (US); Chie Kawahara, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/912,077

(22) Filed: Oct. 26, 2010

(65) Prior Publication Data

US 2011/0046520 A1 Feb. 24, 2011

Related U.S. Application Data

(63) Continuation of application No. 11/733,663, filed on Apr. 10, 2007, now Pat. No. 7,844,336.

(51) Int. Cl.
*A61B 5/11* (2006.01)

(52) U.S. Cl. ......... 607/49; 607/1; 607/2; 607/9; 607/11; 607/17; 607/19; 607/25; 607/30; 607/32; 607/48; 607/60; 607/77; 607/115; 607/116; 600/300; 600/301; 600/508; 600/509; 600/510; 600/515; 600/516; 600/517; 600/518; 600/546; 128/903; 128/920

(58) Field of Classification Search ............ 607/1–2, 607/9, 11, 17, 19, 25, 30, 32, 48–49, 60, 607/77, 115, 116; 600/300–301, 508–510, 600/515–518, 546; 128/903, 920
See application file for complete search history.

(56) References Cited

U.S. PATENT DOCUMENTS

| | | | |
|---|---|---|---|
| 4,846,195 A | 7/1989 | Alt | |
| 4,869,251 A | 9/1989 | Lekholm et al. | |
| 5,010,893 A | 4/1991 | Sholder | |
| 5,031,618 A | 7/1991 | Mullett | |
| 5,233,984 A | 8/1993 | Thompson | |
| 5,330,505 A | 7/1994 | Cohen | |
| 5,354,317 A | 10/1994 | Alt | |
| 5,593,431 A | 1/1997 | Sheldon | |
| 5,725,562 A | 3/1998 | Sheldon | |
| 5,957,957 A | 9/1999 | Sheldon | |

(Continued)

FOREIGN PATENT DOCUMENTS

EP 0804939 A2 11/1997

(Continued)

OTHER PUBLICATIONS

"U.S. Appl. No. 10/892,937, Final Office Action mailed Mar. 11, 2010", 7 pgs.

(Continued)

*Primary Examiner* — Carl H Layno
*Assistant Examiner* — Deborah Malamud
(74) *Attorney, Agent, or Firm* — Schwegman, Lundberg & Woessner, P.A.

(57) ABSTRACT

A system includes an implantable medical device. The implantable medical device includes a control circuit and a motion sensing device. The motion sensing device is coupled to the control circuit, and the motion sensing device is configured to transmit signals to the control circuit. The control circuit is configured to identify one or more steps of a patient using the motion sensing device signal.

20 Claims, 5 Drawing Sheets

U.S. PATENT DOCUMENTS

| | | | |
|---|---|---|---|
| 6,021,352 | A | 2/2000 | Christopherson et al. |
| 6,044,297 | A | 3/2000 | Sheldon et al. |
| 6,045,513 | A | 4/2000 | Stone et al. |
| 6,102,874 | A | 8/2000 | Stone et al. |
| 6,246,910 | B1 | 6/2001 | Bonnet et al. |
| 6,270,457 | B1 | 8/2001 | Bardy |
| 6,273,856 | B1 | 8/2001 | Sun et al. |
| 6,280,409 | B1 | 8/2001 | Stone et al. |
| 6,336,903 | B1 | 1/2002 | Bardy |
| 6,368,284 | B1 | 4/2002 | Bardy |
| 6,398,728 | B1 | 6/2002 | Bardy |
| 6,411,840 | B1 | 6/2002 | Bardy |
| 6,466,821 | B1 | 10/2002 | Pianca et al. |
| 6,473,646 | B2 | 10/2002 | Sun et al. |
| 6,539,249 | B1 | 3/2003 | Kadhiresan et al. |
| 6,572,557 | B2 | 6/2003 | Tchou et al. |
| 6,600,941 | B1 | 7/2003 | Khuri |
| 6,658,292 | B2 | 12/2003 | Kroll et al. |
| 6,694,186 | B2 | 2/2004 | Bardy |
| 6,704,595 | B2 | 3/2004 | Bardy |
| 6,741,885 | B1 | 5/2004 | Park et al. |
| 6,811,537 | B2 | 11/2004 | Bardy |
| 6,826,425 | B2 | 11/2004 | Bardy |
| 6,827,690 | B2 | 12/2004 | Bardy |
| 6,834,436 | B2 | 12/2004 | Townsend et al. |
| 6,887,201 | B2 | 5/2005 | Bardy |
| 6,904,312 | B2 | 6/2005 | Bardy |
| 6,908,437 | B2 | 6/2005 | Bardy |
| 6,913,577 | B2 | 7/2005 | Bardy |
| 6,937,900 | B1 | 8/2005 | Pianca et al. |
| 6,945,934 | B2 | 9/2005 | Bardy |
| 6,952,611 | B2 | 10/2005 | Sun et al. |
| 6,961,615 | B2 | 11/2005 | Kroll et al. |
| 6,974,413 | B2 | 12/2005 | Bardy |
| 6,990,375 | B2 | 1/2006 | Kloss et al. |
| 7,155,281 | B1 | 12/2006 | Fayram |
| 7,171,271 | B2 | 1/2007 | Koh et al. |
| 7,207,945 | B2 | 4/2007 | Bardy |
| 7,210,240 | B2 | 5/2007 | Townsend et al. |
| 7,258,670 | B2 | 8/2007 | Bardy |
| 7,260,436 | B2 | 8/2007 | Kilgore et al. |
| 7,299,087 | B2 | 11/2007 | Bardy |
| 7,302,291 | B2 | 11/2007 | Bardy |
| 7,313,440 | B2 | 12/2007 | Miesel |
| 7,328,131 | B2 | 2/2008 | Donofrio et al. |
| 7,471,290 | B2 | 12/2008 | Wang et al. |
| 7,698,830 | B2 | 4/2010 | Townsend et al. |
| 7,844,336 | B2 | 11/2010 | Fricke et al. |
| 2002/0151936 | A1 | 10/2002 | Kloss et al. |
| 2002/0170193 | A1 | 11/2002 | Townsend et al. |
| 2002/0188332 | A1 | 12/2002 | Lurie et al. |
| 2003/0040776 | A1 | 2/2003 | Kroll et al. |
| 2003/0149453 | A1 | 8/2003 | Kroll et al. |
| 2004/0073128 | A1 | 4/2004 | Hatlestad et al. |
| 2004/0112151 | A1 | 6/2004 | Maxwell et al. |
| 2004/0127807 | A1 | 7/2004 | Hatlesad et al. |
| 2005/0010265 | A1 | 1/2005 | Baru et al. |
| 2005/0126026 | A1 | 6/2005 | Townsend et al. |
| 2005/0245988 | A1 | 11/2005 | Miesel |
| 2007/0115277 | A1 | 5/2007 | Wang et al. |
| 2007/0118056 | A1 | 5/2007 | Wang et al. |
| 2007/0169364 | A1 | 7/2007 | Townsend et al. |
| 2007/0293741 | A1 | 12/2007 | Bardy |
| 2008/0082001 | A1 | 4/2008 | Hatlestad et al. |
| 2008/0255626 | A1 | 10/2008 | Fricke et al. |
| 2009/0024005 | A1 | 1/2009 | Lewicke et al. |
| 2009/0227883 | A1 | 9/2009 | Zhang et al. |
| 2009/0312973 | A1 | 12/2009 | Hatlestad et al. |

FOREIGN PATENT DOCUMENTS

| | | |
|---|---|---|
| EP | 1954192 A2 | 8/2008 |
| WO | WO-9502431 A1 | 1/1995 |
| WO | WO-0189365 A2 | 11/2001 |
| WO | WO-2009110996 A1 | 9/2009 |

OTHER PUBLICATIONS

"U.S. Appl. No. 10/892,937, Non-Final Office Action mailed Feb. 3, 2009", 8 pgs.

"U.S. Appl. No. 10/892,937, Response filed Jun. 11, 2010 to Final Office Action mailed Mar. 11, 2010", 6 pgs.

"U.S. Appl. No. 10/892,937, Response filed May 4, 2009 to Non Final Office Action mailed Feb. 3, 2009", 7 pgs.

"U.S. Appl. No. 11/733,663, Final Office Action mailed May 19, 2010", 8 pgs.

"U.S. Appl. No. 11/733,663, Non-Final Office Action mailed Dec. 10, 2009", 5 pgs.

"U.S. Appl. No. 11/733,663, Notice of Allowance mailed Jul. 23, 2010", 6 pgs.

"U.S. Appl. No. 11/733,663, Response filed Mar. 9, 2010 to Non Final Office Action mailed Dec. 10, 2009", 9 pgs.

"U.S. Appl. No. 11/733,663, Response filed Jun. 22, 2010 to Final Office Action mailed May 19, 2010", 11 pgs.

"International Application Serial No. PCT/US2009/001314, International Search Report mailed Jul. 20, 2009", 4 pgs.

"International Application Serial No. PCT/US2009/001314, Written Opinion mailed Jul. 20, 2009", 7 pgs.

Arvanitakis, Z., et al., "Diabetes mellitus and progression of rigidity and gait disturbance in older persons", Neurology, 63(6), (2004), 996-1001.

Evangelista, Lorraine S., et al., "Validity of Pedometers for Measuring Exercise Adherence in Heart Failure Patients", Journal of Cardiac Failure, 11(5), (2005), 366-71.

Fleg, J. L, et al., "Assessment of functional capacity in clinical and research applications: An advisory from the Committee on Exercise, Rehabilitation, and Prevention, Council on Clinical Cardiology, American Heart Association", Circulation, 102(13), (Sep. 26, 2000), 1591-7.

Hunt, S. A, et al., "ACC/AHA Guidelines for the Evaluation and Management of Chronic Heart Failure in the Adult: Executive Summary a Report of the American College of Cardiology/American Heart Association Task Force on Practice Guidelines", Circulation., 104(24), (Dec. 11, 2001), 2996-3007.

Mai, J., et al., "Posture Detection Algorithm Using Multi Axis DC Accelerometer", PACE, vol. 22 (Part II), (Abstract #605), (Apr. 1999), p. 851.

Mancini, D. M., et al., "Value of peak exercise oxygen consumption for optimal timing of cardiac transplantation in ambulatory patients with heart failure", Circulation, 83(3), (1991), 778-86.

Schneider, Patrick L, et al., "Accuracy and reliability of 10 pedometers for measuring steps over a 400-m walk", Medicine and Science in Sports and Exercise, 35(10), (2003), 1779-1784.

Schneider, Patrick L, et al., "Pedometer measures of Free-Living Physical Activity: Comparison of 13 Models", Medicine and Science in Sports and Exercise, 36(2), (2004), 331-335.

Thompson, D. L, et al., "Relationship between Accumulated Walking and body Composition in Middle-Aged Women", Medicine and Science in Sports and Exercise, 36(5), (2004), 911-914.

Walsh, J T, et al., "Relation of daily activity levels in patients with chronic heart failure to long-term prognosis", Am J Cardiol, 79(10), (1997), 1364-1369.

Weber, K. T., et al., "Oxygen utilization and ventilation during exercise in patients with chronic cardiac failure", Circulation, 65(6), (Jun. 1982), 1213-23.

"Abbott Diagnostics—Heart Failure", Abbott Laboratories, Abbott Park Illinois, (2011), 8 pgs.

"U.S. Appl. No. 10/892,937, Final Office Action mailed Oct. 13, 2011", 6 pgs.

"U.S. Appl. No. 10/892,937, Non-Final Office Action mailed Apr. 28, 2011", 6 pgs.

"U.S. Appl. No. 10/892,937, Notice of Allowance mailed Jan. 25, 2012", 5 pgs.

"U.S. Appl. No. 10/892,937, Response filed Jan. 13, 2012 to Final Office Action mailed Oct. 13, 2011", 5 pgs.

"U.S. Appl. No. 10/892,937, Response filed Aug. 29, 2011 to Non-Final Office Action mailed Apr. 28, 2011", 6 pgs.

"U.S. Appl. No. 12/396,196, Decision on Pre-Appeal Brief mailed Dec. 7, 2011", 2 pgs.

"U.S. Appl. No. 12/396,196, Final Office Action mailed Aug. 2, 2011", 9 pgs.

"U.S. Appl. No. 12/396,196, Non-Final Office Action mailed Mar. 11, 2011", 8 pgs.

"U.S. Appl. No. 12/396,196, Pre-Appeal Brief Request filed Oct. 3, 2011", 5 pgs.

"U.S. Appl. No. 12/396,196, Response filed Jun. 13, 2011 to Non-Final Office Action mailed Mar. 11, 2011", 10 pgs.

"U.S. Appl. No. 12/425,195, Ex Parte Quayle Action mailed Oct. 12, 2011", 14 pgs.

"U.S. Appl. No. 12/425,195, Notice of Allowance mailed Dec. 19, 2011", 11 pgs.

IMPLANTABLE MEDICAL DEVICE CONFIGURED AS A PEDOMETER

CROSS-REFERENCE TO RELATED APPLICATIONS

This application is a Continuation of U.S. Application Ser. No. 11/733,663, filed on Apr. 10, 2007, now issued as U.S. Pat. No. 7,844,336, the benefit of priority of which is claimed herein, and which is incorporated herein by reference in its entirety.

TECHNICAL FIELD

This document pertains generally to implantable medical devices, and more particularly, but not by way of limitation, to implantable medical devices configured as a pedometer.

BACKGROUND

Implantable medical devices include, among other devices, cardiac rhythm management devices. Such implantable medical devices can include a motion sensing device such as an accelerometer, a tilt switch, or a mercury switch, and the motion sensing device can be used to detect and monitor the physical activity of a patient. This physical activity data has been used to modulate a pacing rate as a function of a patient's physical activity. However, many times the activity data generated by a motion sensing device associated with an implantable medical device is cryptic and difficult to interpret.

OVERVIEW

This overview is intended to provide an overview of the subject matter of the present patent application. It is not intended to provide an exclusive or exhaustive explanation of the invention. The detailed description is included to provide further information about the subject matter of the present patent application.

In Example 1, a system includes an implantable medical device. The implantable medical device includes a control circuit and a motion sensing device, coupled to the control circuit, the motion sensing device configured to transmit a signal to the control circuit. The control circuit is configured to identify one or more steps of a patient using the motion sensing device signal.

In Example 2, the motion sensing device of Example 1 optionally includes an accelerometer.

In Example 3, the systems of Examples 1-2 optionally include a telemetry circuit, the telemetry circuit coupled to the control circuit for communicating to an external device.

In Example 4, the systems of Examples 1-3 optionally include the external device, wherein the external device is a local external device; and further wherein the local external device is configured to communicate with a remote external device.

In Example 5, at least one of the implantable medical device and the external device of Examples 1-4 are optionally configured to calculate, using data about the one or more steps of the patient, at least one of a count of the one or more steps of the patient, a count of the one or more steps of the patient during a particular period of time, a physical activity category, a distance traveled by the patient during a particular period of time, an amount of time spent walking by the patient during a particular period of time, a caloric expenditure by the patient during a particular period of time, an amount of time between episodes of walking, a stride pattern of the patient, a measure of activity of the patient, a velocity of the patient, a length of a particular step, and an amount of time relating to a duration of the particular step.

In Example 6, the systems of Examples 1-5 optionally include an electrical stimulation circuit coupled to the control circuit, the electrical stimulation circuit configured to deliver at least one electrical pulse using data about the one or more steps of the patient.

In Example 7, the data about the one or more steps of the patient of Examples 1-6 are optionally used to initiate or adjust at least one of an AV delay, a current pacing rate, a baseline pacing rate, an upper limit of a pacing rate, and an acceleration of a pacing rate.

In Example 8, the control circuit of Examples 1-7 is optionally configured to confirm a single step by identifying a first step followed by a second step within a particular period of time.

In Example 9, the control circuit of Examples 1-8 is optionally configured to confirm a single step by identifying three consecutive steps.

In Example 10, the accelerometer of Examples 1-9 optionally includes a three axis accelerometer, and the control circuit is optionally configured to identify a step up by the patient, a step down by the patient, and a step forward by the patient.

In Example 11, the systems of Examples 1-10 optionally include a drug titration circuit, the drug titration circuit configured to deliver a drug using data about the one or more steps of the patient.

In Example 12, the systems of Examples 1-11 optionally include an alert circuit coupled to the control circuit, the alert circuit configured to provide an alert using data about the one or more steps of the patient.

In Example 13, the control circuit of Examples 1-12 optionally include a circuit to identify the one or more steps of the patient by one or more of identifying a peak in an output of the accelerometer and by pattern matching an output of the accelerometer.

In Example 14, a process includes receiving data from an implantable motion sensing device, and processing the data to identify one or more steps taken by a patient.

In Example 15, the motion sensing device of Example 14 optionally includes an accelerometer.

In Example 16, the processes of Examples 14-15 optionally include transmitting the data from the implantable motion sensing device to an external device, and displaying the data about the one or more steps taken by the patient on the external device.

In Example 17, the processes of Examples 14-16 optionally include transmitting the data about the one or more steps taken by the patient to an external device, and displaying the data about the one or more steps taken by the patient on the external device. The processing the data to identify the one or more steps taken by the patient optionally occurs on the external device.

In Example 18, the processes of Examples 14-17 optionally include using the data about the one or more steps taken by the patient to calculate at least one of a number of steps taken by the patient, a number of steps taken by the patient during a particular time period, a physical activity category, a caloric expenditure by the patient, a stride pattern of the patient, a measure of activity of the patient, a velocity of the patient, a length of a time interval between episodes of walking by the patient, a time duration of an episode of walking of the patient, a distance covered by the patient, a measure of sustained steps during a period of time, and a gait of the patient.

In Example 19, the processes of Examples 14-18 optionally include identifying a step by identifying three or more consecutive steps.

In Example 20, the processes of Examples 14-19 optionally include identifying a step by identifying a first step followed by a second step within a particular period of time.

In Example 21, the processes of Examples 14-20 optionally include a disease progression of a patient using the data about the one or more steps taken by the patient.

In Example 22, the processes of Examples 14-21 optionally include generating an alert using the data about the one or more steps taken by the patient.

In Example 23, the processes of Examples 14-22 optionally include altering an operation of an implantable medical device using the data about the one or more steps taken by the patient.

In Example 24, the processes of Examples 14-23 optionally include identifying the data about the one or more steps taken by the patient by one or more of identifying a peak in an output of the accelerometer and by pattern matching the output of the accelerometer.

In Example 25, the processes of Examples 14-24 optionally include categorizing a patient into a physical activity category using the data about the one or more steps taken by the patient.

In Example 26, the processes of Examples 14-25 optionally include identifying a first step, starting a timer, and inhibiting an identification of a second step until after expiration of the timer.

In Example 27, the processes of Examples 14-26 optionally include evaluating patient compliance using the data about the one or more steps taken by the patient.

In Example 28, the patient compliance of Examples 14-27 optionally relates to a patient exercise program.

In Example 29, the processes of Examples 14-28 optionally include identifying a step up by the patient, a step down by the patient, and a step forward by the patient.

In Example 30, a system includes an implantable medical device, the implantable medical device including a control circuit, a motion sensing device, coupled to the control circuit, the motion sensing device configured to transmit a signal to the control circuit, and a telemetry circuit, coupled to the control circuit, and configured to transmit a signal to an external device. The external device is configured to identify one or more steps of a patient using the signal from the implantable medical device.

In Example 31, the system of Example 30 optionally includes the external device.

In Example 32, the motion sensing device of Examples 30-31 optionally includes an accelerometer.

BRIEF DESCRIPTION OF THE DRAWINGS

In the drawings, which are not necessarily drawn to scale, like numerals may describe substantially similar components in different views Like numerals having different letter suffixes may represent different instances of substantially similar components. The drawings illustrate generally, by way of example, but not by way of limitation, various examples discussed in the present document.

DETAILED DESCRIPTION

The following detailed description includes references to the accompanying drawings, which form a part of the detailed description. The drawings show, by way of illustration, specific embodiments in which the invention may be practiced. These embodiments are also referred to herein as "examples." The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one, independent of any other usages of "at least one" or "one or more." In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
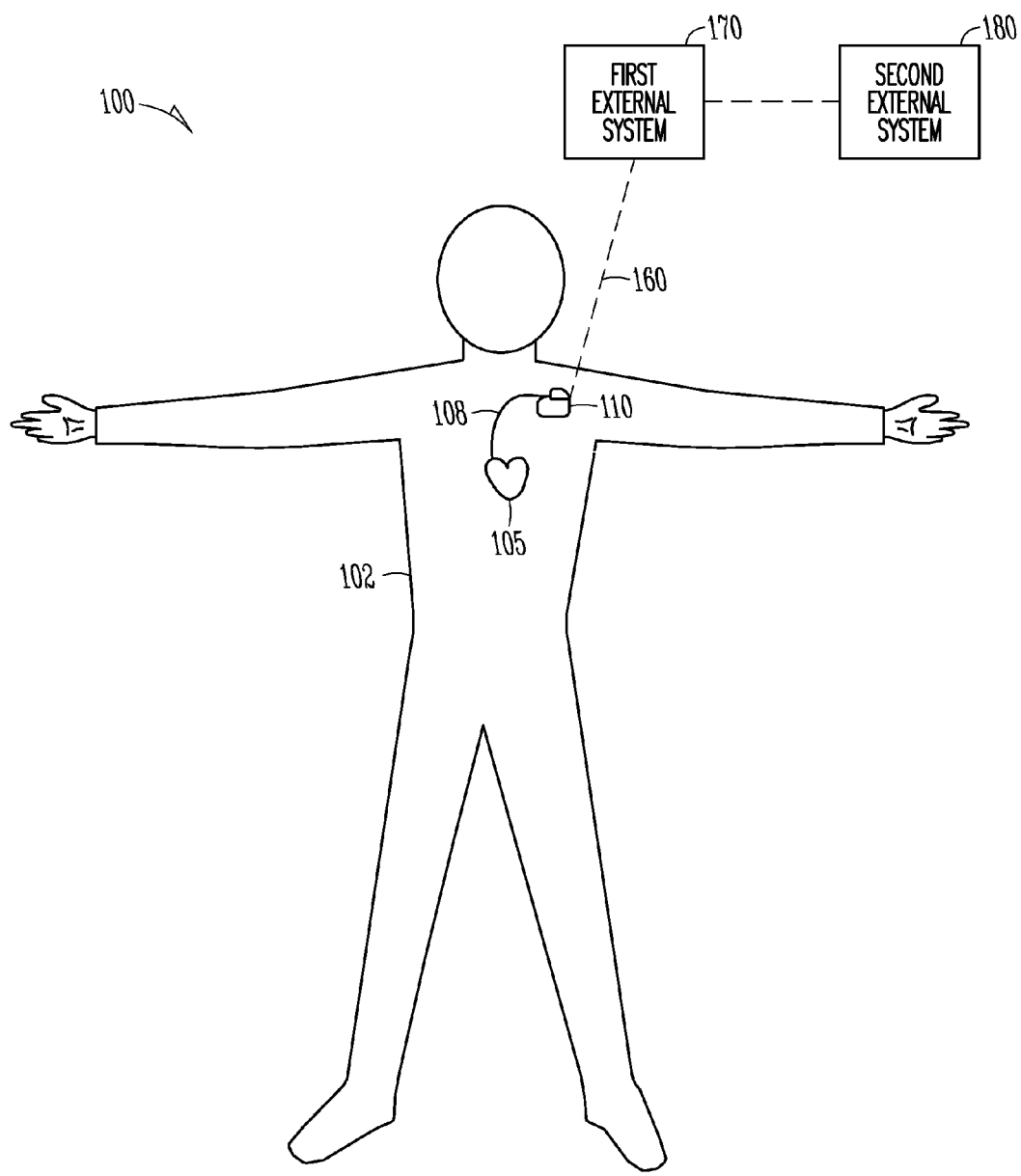
FIG. 1 illustrates an example of an implanted medical device in communication with an external device via a telemetry system.

FIG. 1 is a diagram illustrating an example of a medical device system 100, and portions of an environment in which it is used. The environment includes a body 102 with a heart 105. System 100 includes an implantable medical device 110, a lead system 108, a first adjunct device or external system 170, a second adjunct device or external system 180, and a wireless telemetry link 160. The first external system 170 can be referred to as a local external system, and the second external system 180 can be referred to as a remote external system. Heart rate data, pacing data, EGM data, motion sensing device data (e.g., accelerometer data), and other data can be transferred from the device 110 to the external system 170 via the telemetry link 160. The telemetered data loaded into the device 170 can then be used for analysis and interpretation either immediately or at a later time.

Figure 2:
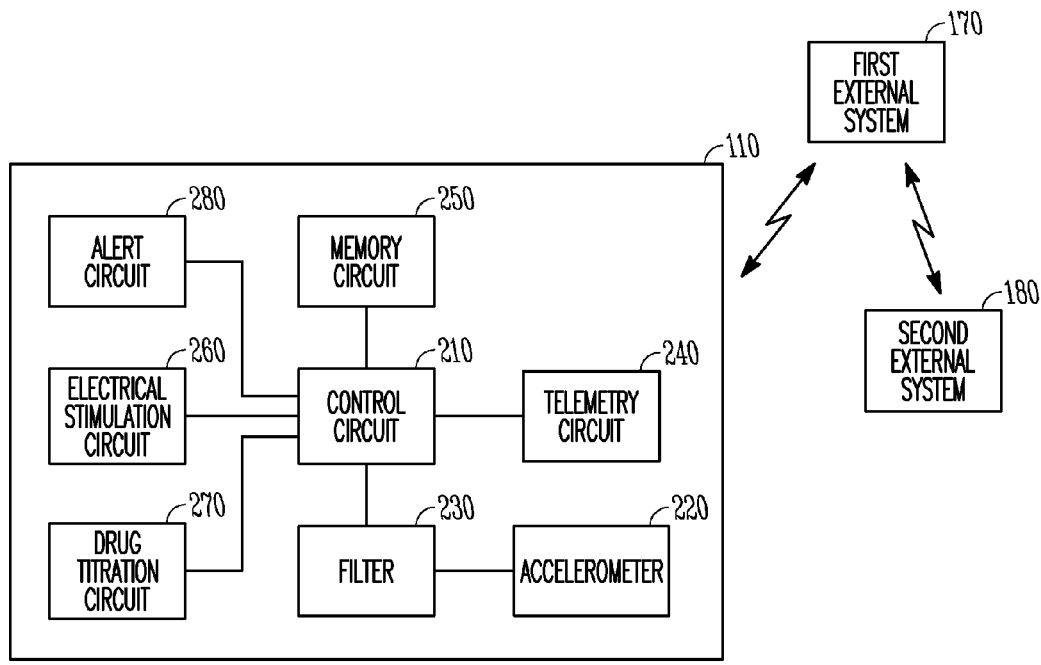
FIG. 2 illustrates an example of a block diagram of an implantable medical device.

FIG. 2 illustrates an example of the implantable medical device 110 of FIG. 1. The device 110 includes a control circuit 210 and an accelerometer 220. While FIG. 2 illustrates an example device 110 as including an accelerometer, other motion sensing devices such as a mercury switch could also be used. In systems in which an accelerometer is present, the accelerometer could be a 1-axis, 2-axis, or 3-axis accelerometer. For ease of explanation, examples of the device 110 described herein will be described as having an accelerometer.

In an example, an anti-aliasing or other filter 230 is located between the control circuit 210 and the accelerometer 220. An amplifier could also be placed between the control circuit 210 and the accelerometer 220. A telemetry circuit 240, a memory circuit 250, an electrical stimulation circuit 260, a drug titration circuit 270, or an alert circuit 280 can be connected to the control circuit 210.

Figure 3:
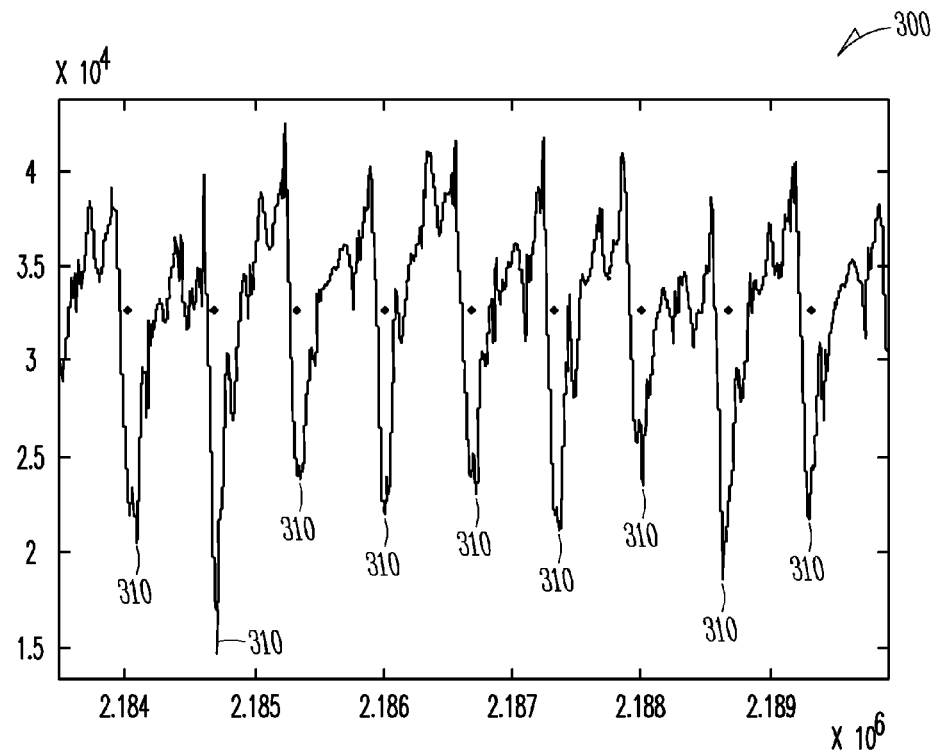
FIG. 3 illustrates an example output of an accelerometer.

The memory circuit 250 can be configured to store data about the one or more steps of a patient. The data can include an accelerometer trace as illustrated in FIG. 3. The accelerometer trace 300 includes information such as the amplitude of a peak associated with a step (such an amplitude is normally less for a step up than a normal step or a step down), an interval between steps, and a duration of a step.

In an example system, the implantable medical device 110 can be a cardiac rhythm management device. In another example system, the telemetry circuit 240 can be configured to communicate with the external system 170. The external system 170 can be a local external system. The local external system can be attachable to a patient's body, or it can be a system that is separate from a patient's body. The external device can also be a remote external device, such as a device to which a patient's physician can have access. In a system with a remote external device, a local external device is configured to communicate with the remote external device.

FIG. 3 illustrates an example trace 300 of an implantable accelerometer output generated by a patient walking on a treadmill at a speed of approximately 2 mph. The trace 300 includes several peaks (valleys) or depressions 310 that are caused by the patient's foot coming in contact with the treadmill surface during the test. These depressions 310 can be referred to as footfalls, and the control circuit can be configured to identify the depressions 310, and consequently identify each step that a patient takes. This identification of the depressions 310 can be a function of amplitude, morphology, or a combination of amplitude and morphology. This analysis of the depressions 310 can be performed in the control circuit 210, the external device 170, or the external device 180.

Figure 4:
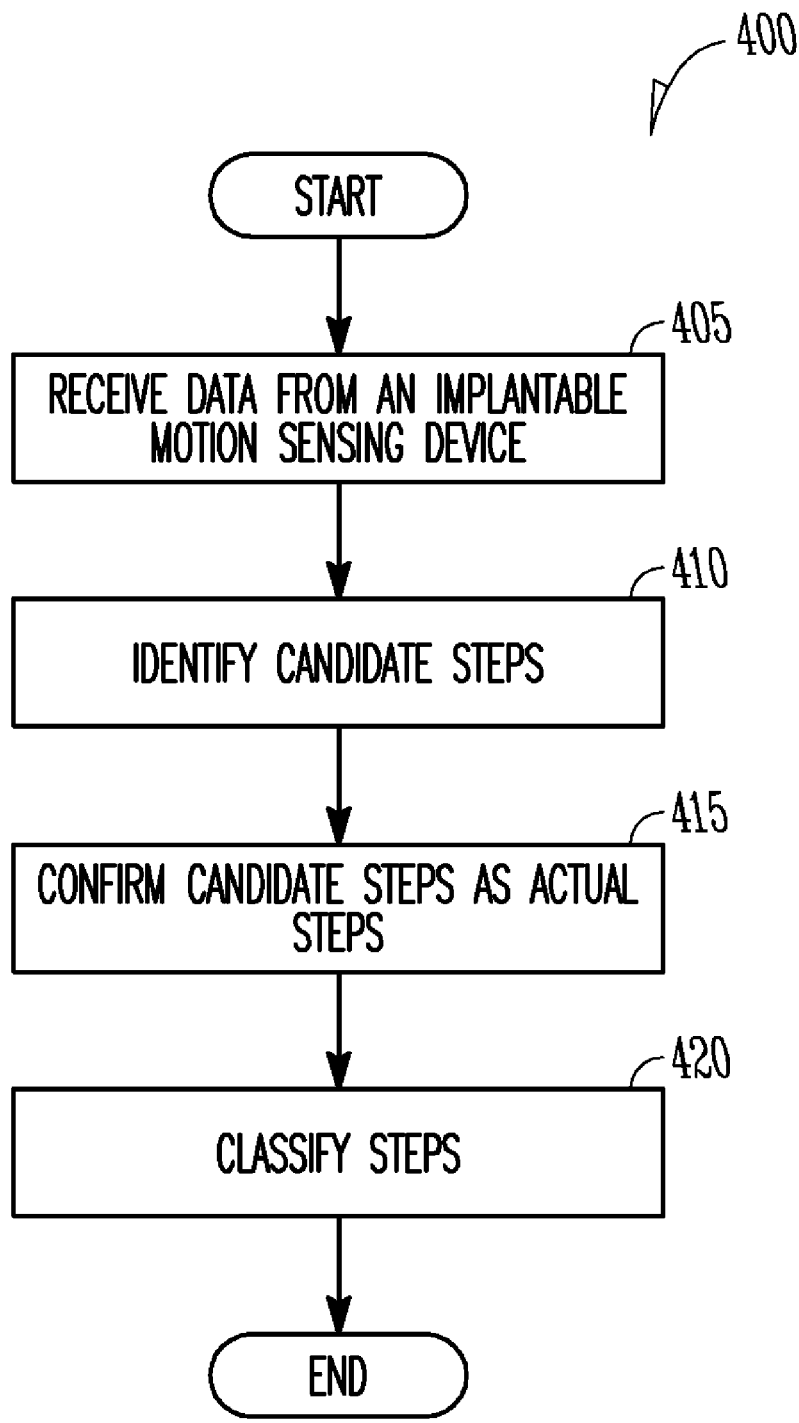
FIG. 4 illustrates an example flowchart of a process to identify steps of a patient using an implantable medical device.

FIG. 4 illustrates an example flowchart of a process 400 to identify steps of a patient using an implantable medical device such as the implantable medical device 110 of FIG. 2. The operations illustrated in FIG. 4 need not all be executed in each example implantable medical device system, and the operations need not be executed in the order as illustrated in FIG. 4. At 405, data is received from an implantable motion sensing device, such as an implantable accelerometer. At 410, candidate patient steps are identified. At 415, the identified candidate steps are confirmed as actual patient steps. At 420, a step is classified. For example, a step can be classified as a step up, a step down, or a step forward.

Figure 5:
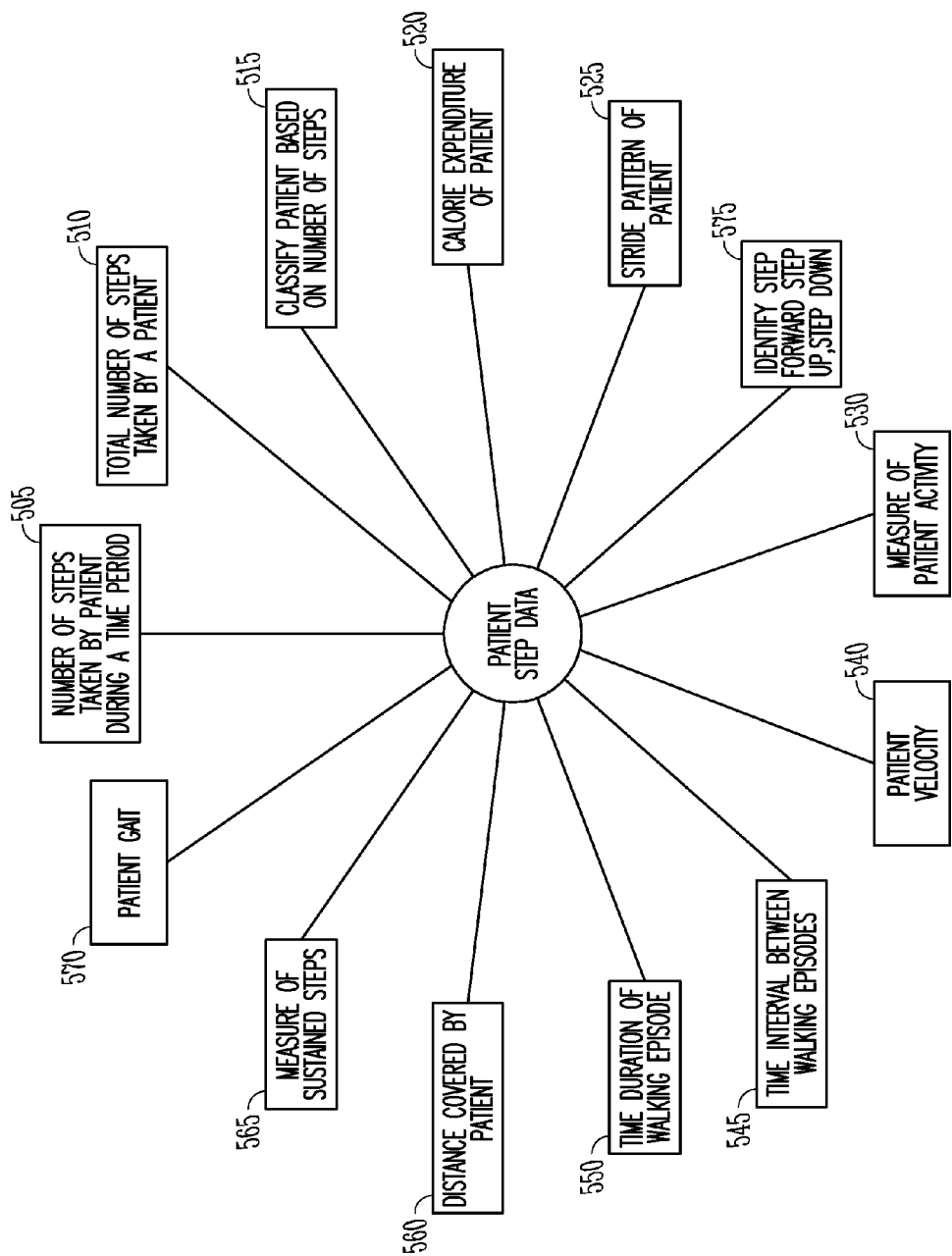
FIG. 5 illustrates several measurements that can be calculated using patient step data.

The data about the one or more steps taken by the patient are used to calculate several measures associated with the patient. FIG. 5 illustrates that these measures can include a number of steps taken by the patient during a particular time period (505), a total number of steps taken by the patient without regard to a time period (510), a classification of the patient based on the number of steps taken by the patient (515), a caloric expenditure of the patient (520), a stride pattern of the patient (525), a measure of activity of the patient (530), a velocity of the patient (540), a length of a time interval between episodes of walking by the patient (545), a time duration of an episode of walking by the patient (550), a distance covered by the patient (560), a measure of sustained steps during a period of time (565), and a gait of the patient (570). At 575, a three-axis accelerometer 220 in an implantable medical device 110 can identify a step up by the patient, a step down by the patient, and a step forward by the patient.

Such data can be used by a physician to monitor patient compliance, general health status of a patient, or the progression or regression of a diseased patient.

As indicated above, a patient can be classified into a group based on the number of steps that that patient takes during a day. In an example, the group includes a physical activity category. One such classification system has been developed by the New York Heart Association (NYHA). A similar system could be developed based on the number of steps that a patient takes in a day. For example, a patient who takes more than 10,000 steps per day could be identified as a class I patient. A class I patient may not be limited in any activities, and may suffer no symptoms from ordinary activities. A patient who takes between 5,000 and 7,000 steps per day could be identified as a class II patient. A class II patient may be mildly limited in activities, and may be comfortable with rest or mild exertion. A patient who takes between 3,000 and 5,000 steps per day could be identified as a class III patient. A class III patient may experience a marked limitation of activity, and a class III patient may only be comfortable when at rest. A patient who takes less than 1,000 steps per day could be identified as a class IV patient. A class IV patient should be at complete rest in a bed or a chair. Any physical activity may bring on discomfort for a class IV patient, and symptoms may occur in a class IV patient at rest.

The caloric expenditure can be calculated by first using the number of steps taken by a patient to determine the distance traveled by the patient, and then using the weight of the patient, calculating the caloric expenditure of the patient by one of several methods known in the art. In an example system, a change in the gait or stride pattern of a patient can be noted by saving data relating to the stride or gait of a patient in the memory circuit 250, such as the average time between footfalls, and thereafter comparing current stride and gait data with the patient's historical data. In another example system, the length of the patient's stride can be calculated and recalculated based on the time between footfalls.

Figure 6:
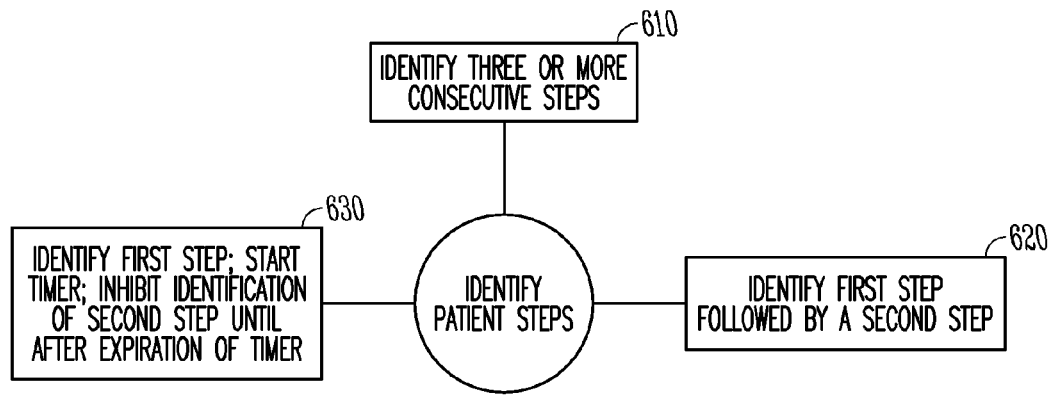
FIG. 6 illustrates several methods to verify an actual patient step.

FIG. 6 illustrates that the control circuit 210, the external system 170, or the external system 180 can execute one or more of several procedures that help assure that only steps of a patient are identified (and not some other activity, disturbance, or noise), and that a step is counted only once. In one example, at 610, a step is identified as a step when the control circuit 210, the external system 170, or the external system 180 identifies three or more consecutive steps. This can be accomplished by identifying three consecutive depressions 310 in FIG. 3 within a time frame wherein a patient would take three consecutive steps. If three depressions 310 are not identified in that time frame, then data in that time frame is not identified as a step. In another example, at 620, the control circuit 210, the external system 170, or the external system 180 identifies a step by identifying a first step that is followed by a second step within a particular period of time. The period of time can be set on a patient by patient basis by testing the patient and determining the average time between footfalls of the patient during normal walking of the patient.

In another example system, at 630, the control circuit 210, the external system 170, or the external system 180 identifies a first step (via the detection of a depression 310 (i.e., a footfall)), starts a timer, and then inhibits the identification of a second step until after expiration of the timer. The timer can be a dynamic timer, such that as the pace of a patient's walking increases, the timer window is shortened to compensate for the increased walking pace. The use of a timer in this manner prevents counting a single step as more than one step, or interpreting noise in the system as a step.

Figure 7:
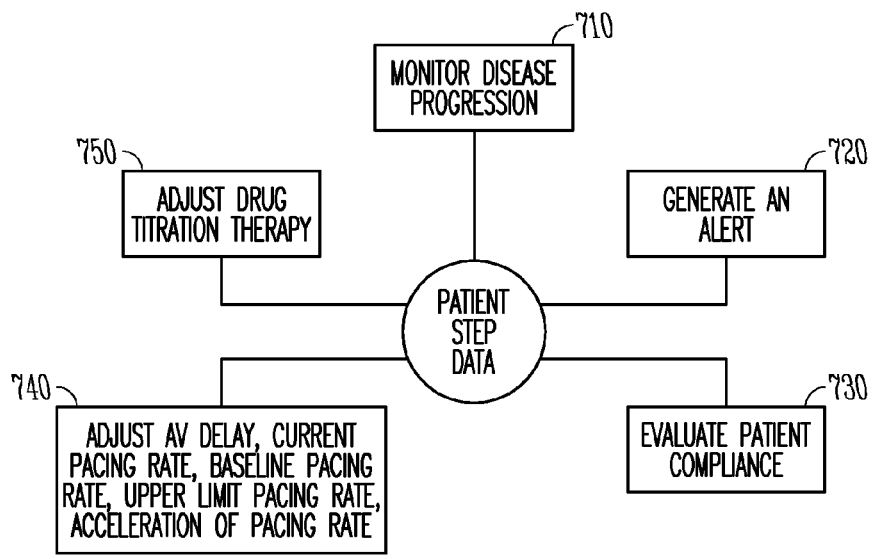
FIG. 7 illustrates several actions that can be taken using patient step data.

FIG. 7 illustrates several functions that an implantable medical device can implement using patient step data. At 710, a disease progression of a patient can be monitored using the data about the one or more steps taken by the patient. For example, if the number of steps taken by a patient per day decreases over a period of time, that can be indicative of a worsening of the patient's condition. In connection with the worsening of the patient's condition, it can also be noted whether a patient has moved from one physical activity category to another physical activity category.

At 720, the alert circuit 280, the external system 170, or the external system 180 can generate an alert using the data about the one or more steps taken by the patient. This alert can be for the benefit of the patient to inform that patient that he is either hyperactive for his particular condition, hypoactive for his particular condition, or as an indication that his condition is worsening. The alert can also be for the benefit of the patient's physician, and can serve as general information regarding how the patient is progressing or digressing, or can indicate a more dire situation such a substantial decrease in the patient's number of steps taken over a time period indicating a worsening of the patient's condition. At 730, a physician or other health care provider can use the patient step data to evaluate patient compliance. For example, if a patient has been instructed to exercise by walking a certain distance per day, or the patient has been instructed to rest and recover, the patient's compliance with those instructions can be determined at the external system 170 or the external system 180 using the patient step data.

At 740, the control circuit 210 alters an operation of the implantable medical device 110 using the data about the one or more steps taken by the patient. For example, if the implantable medical device 110 is a cardiac rhythm management device having an electrical stimulation circuit 260, the control circuit 210 could alter an AV delay, a current pacing rate, a baseline pacing rate, an upper limit of the pacing rate (by lowering it or raising it in response to the patient step data), or an acceleration of the current pacing rate. As another example, at 750, if the implantable medical device 110 includes a drug delivery circuit 270, an operation of the drug delivery circuit could be altered by the control circuit 210 using the patient step data. If the drug delivery circuit 270 delivers insulin to the patient, the rate or level of insulin delivery can be modified based using the patient step data. For example, if a patient is taking more steps over a particular period of time than is normal for that patient, the drug delivery circuit 270 can increase the rate or level of insulin delivery in response to the increase in steps taken by the patient.

The above description is intended to be illustrative, and not restrictive. For example, the above-described embodiments (or one or more aspects thereof) can be used in combination with each other. Other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
an implantable cardiac rhythm management device comprising:
a control circuit; and
a motion sensing device coupled to the control circuit, the motion sensing device configured to transmit a signal to the control circuit;
wherein the control circuit is configured to:
identify a candidate step of a patient using the motion sensing device signal; and
confirm that the candidate step is an actual individual step of the patient.

2. The system of claim 1, wherein the motion sensing device includes an accelerometer.

3. The system of claim 2, wherein the accelerometer comprises a three-axis accelerometer, and wherein the control circuit is configured to classify the actual individual step as one of a step up by the patient, a step down by the patient, and a step forward by the patient.

4. The system of claim 2, wherein the control circuit comprises a circuit to identify one or more actual individual steps of the patient by one or more of identifying a peak in an output of the accelerometer and by pattern matching an output of the accelerometer.

5. The system of claim 1, comprising an external device communicatively coupled to the implantable cardiac rhythm management device.

6. The system of claim 5, wherein the external device is a local external device configured to communicate with a remote external device.

7. The system of claim 5, wherein at least one of the implantable cardiac rhythm management device and the external device are configured to determine, using data from one or more actual individual steps of the patient, at least one of:
a count of the one or more steps of the patient;
a count of the one or more steps of the patient during a particular period of time;
a physical activity category;
a distance traveled by the patient during a particular period of time;
an amount of time spent walking by the patient during a particular period of time;
a caloric expenditure by the patient during a particular period of time;
an amount of time between episodes of walking;
a stride pattern of the patient;
a measure of activity of the patient;
a velocity of the patient;
a length of a particular step; and
an amount of time relating to a duration of the particular step.

8. The system of claim 1, comprising an electrical stimulation circuit coupled to the control circuit, the electrical stimulation circuit configured to deliver an electrical pulse, wherein delivery of the electrical pulse is based on data from one or more actual individual steps of the patient.

9. The system of claim 1, wherein the control circuit is configured to confirm that the candidate step is an actual individual step of the patient by identifying a first step followed by a second step within a particular period of time.

10. The system of claim 1, wherein the control circuit is configured to confirm that the candidate step is an actual individual step of the patient by identifying three consecutive steps.

11. A method comprising:
  receiving data from an implantable motion sensing device associated with an implantable cardiac rhythm management device; and
  processing the data to:
    identify a candidate step taken by a patient; and
    confirm that the candidate step is an actual individual step of the patient.

12. The method of claim 11, comprising classifying the actual individual step as one of a step up by the patient, a step down by the patient, and a step forward by the patient using the data from the implantable motion sensing device, wherein the implantable motion sensing device includes an accelerometer.

13. The method of claim 11, wherein processing the data includes identifying one or more actual individual steps of the patient by one or more of identifying a peak in an output of an accelerometer of the implantable motion sensing device and by pattern matching an output of the accelerometer.

14. The method of claim 11, comprising:
  transmitting the data from the implantable motion sensing device to an external device; and
  displaying the data about the one or more steps taken by the patient on the external device.

15. The method of claim 11, comprising using data about one or more actual individual steps taken by the patient to determine at least one of:
  a number of steps taken by the patient;
  a number of steps taken by the patient during a particular time period;
  a physical activity category;
  a caloric expenditure by the patient;
  a stride pattern of the patient;
  a measure of activity of the patient;
  a velocity of the patient;
  a length of a time interval between episodes of walking by the patient;
  a time duration of an episode of walking of the patient;
  a distance covered by the patient;
  a measure of sustained steps during a period of time; and
  a gait of the patient.

16. The method of claim 11, wherein processing the data includes confirming that the candidate step is an actual individual step by identifying three or more consecutive steps.

17. The method of claim 11, wherein processing the data includes confirming that the candidate step is an actual individual step by identifying a first step followed by a second step within a particular period of time.

18. A system comprising:
  an implantable cardiac rhythm management device comprising:
    a control circuit;
    a motion sensing device coupled to the control circuit, the motion sensing device configured to transmit a signal to the control circuit; and
    a telemetry circuit, coupled to the control circuit, and configured to transmit a signal to an external device;
  wherein the external device is configured to;
    identify a candidate step of a patient using the motion sensing device signal; and
    confirm that the candidate step is an actual individual step of the patient.

19. The system of claim 18, wherein the external device is configured to confirm that the candidate step is an actual individual step of the patient by identifying a first step followed by a second step within a particular period of time.

20. The system of claim 18, wherein the external device is configured to confirm that the candidate step is an actual individual step of the patient by identifying three consecutive steps.

* * * * *